US007744904B1

(12) United States Patent
Singh et al.

(10) Patent No.: US 7,744,904 B1
(45) Date of Patent: Jun. 29, 2010

(54) STABILIZATION OF *CLOSTRIDIUM BOTULINUM* NEUROTOXIN COMPLEX

(75) Inventors: Bal Ram Singh, Dartmouth, MA (US); Andrew M. Ress, Boca Raton, FL (US)

(73) Assignee: B.B. Scientific L.L.C., Boca Raton, FL (US)

( * ) Notice: Subject to any disclaimer, the term of this patent is extended or adjusted under 35 U.S.C. 154(b) by 0 days.

(21) Appl. No.: 11/525,566

(22) Filed: Sep. 21, 2006

Related U.S. Application Data

(60) Provisional application No. 60/720,854, filed on Sep. 26, 2005.

(51) Int. Cl.

| | |
|---|---|
| ***A61K 39/02*** | (2006.01) |
| ***A61K 39/08*** | (2006.01) |
| ***A61K 9/36*** | (2006.01) |
| ***A61K 9/14*** | (2006.01) |
| ***A61K 9/16*** | (2006.01) |
| ***A61K 9/50*** | (2006.01) |

(52) U.S. Cl. ................. 424/236.1; 424/247.1; 424/479; 424/480; 424/488; 424/493; 424/499

(58) Field of Classification Search ................... 435/43, 435/47, 127; 424/184.1, 234.1, 236.1, 247.1
See application file for complete search history.

(56) References Cited

U.S. PATENT DOCUMENTS

| | | | | |
|---|---|---|---|---|
| 5,134,127 | A | 7/1992 | Stella et al. | 514/58 |
| 5,696,077 | A * | 12/1997 | Johnson et al. | 514/2 |
| 5,756,468 | A * | 5/1998 | Johnson et al. | 514/21 |
| 6,699,505 | B2 * | 3/2004 | Shastri et al. | 424/486 |
| 6,699,966 | B1 | 3/2004 | Singh et al. | 530/350 |
| 6,818,662 | B2 * | 11/2004 | Ito et al. | 514/361 |
| 7,097,835 | B2 * | 8/2006 | Chalupa et al. | 424/130.1 |
| 2003/0118598 | A1 | 6/2003 | Hunt | 424/184.1 |
| 2004/0126827 | A1 | 7/2004 | Singh et al. | 435/7.32 |
| 2006/0099227 | A1 | 5/2006 | Hunt | 424/239.1 |

FOREIGN PATENT DOCUMENTS

| | | |
|---|---|---|
| EP | 1398038 A1 | 1/2007 |
| WO | WO 85/02767 | 7/1985 |

OTHER PUBLICATIONS

Loftsson et al (Journal of Pharmaceutical Sciences Oct. 1996, vol. 85, No. 10, pp. 1017-1025).*

* cited by examiner

*Primary Examiner*—Vanessa L. Ford
(74) *Attorney, Agent, or Firm*—Winston & Strawn LLP

(57) ABSTRACT

A stable composition including *botulinum* neurotoxin and a cyclodextrin and a method of preserving *botulinum* neurotoxin and for producing a *botulinum* neurotoxin composition with improved stability properties in an efficient and economically advantageous manner. The invention seeks to alleviate the problems associated with rapid degradation or denaturation of *botulinum* neurotoxin by providing a novel composition that exhibits improved stability properties. The *botulinum* neurotoxin is preferably stabilized by forming a cyclodextrin inclusion complex.

13 Claims, 16 Drawing Sheets

23-WEEK INCUBATION OF BOTULINUM NEUROTOXIN TYPE A WITH α, β, AND γ-CYCLODEXTRINS AT 4°C

4-Degree Incubation

| | Wk. 1 | Wk. 2 | Wk. 3 | Wk. 4 | Wk. 12 | Wk. 23 |
|---|---|---|---|---|---|---|
| Control | 100 | 100 | 100 | 100 | 100 | 100 |
| Alpha | 99.47333333 | 99.67 | 99.67333333 | 100 | 100 | 96.21 |
| Beta | 100 | 100 | 100 | 100 | 100 | 93.78 |
| Gamma | 100 | 100 | 100 | 99.78 | 100 | 98.03 |

Incubation Period

CHROMATOGRAM OF α AND β CYCLODEXTRIN INCUBATED BOTULINUM NEUROTOXIN TYPE A AT 4° C

CHROMATOGRAM OF α AND β CYCLODEXTRIN INCUBATED BOTULINUM NEUROTOXIN TYPE A

23-WEEK INCUBATION OF BOTULINUM NEUROTOXIN TYPE A WITH $\alpha,\beta$, AND $\gamma$-CYCLODEXTRINS AT ROOM TEMPERATURE Room Temperature Incubation

| | Wk. 1 | Wk. 2 | Wk. 3 | Wk. 4 | Wk. 12 | Wk. 23 |
|---|---|---|---|---|---|---|
| Control | 100 | 77.02333333 | 68.81 | 55.38333333 | 52.65666667 | 56.14 |
| Alpha | 98.78 | 99.41 | 94.71333333 | 83.27 | 58.65333333 | 51.67333 |
| Beta | 100 | 84.09666667 | 57.75 | 44.53 | 40.10666667 | 35.35 |
| Gamma | 99.80333333 | 100 | 87.30333333 | 74.36 | 54.63666667 | 45.12333 |

Incubation Period

CHROMATOGRAM OF α AND β CYCLODEXTRIN INCUBATED BOTULINUM NEUROTOXIN TYPE A AT ROOM TEMPERATURE

CHROMATOGRAM OF α AND β CYCLODEXTRIN INCUBATED BOTULINUM NEUROTOXIN TYPE A AT ROOM TEMPERATURE

CHROMATOGRAM OF α AND β CYCLODEXTRIN INCUBATED BOTULINUM NEUROTOXIN TYPE A AT ROOM TEMPERATURE

CHROMATOGRAMS OF INCUBATED BOTULINUM NEUROTOXIN AT ROOM TEMP.

CHROMATOGRAM OF α AND β CYCLODEXTRIN INCUBATED BOTULINUM NEUROTOXIN TYPE A AT 4° C

SNAP 25 CLEAVAGE BY TYPE A
COMPLEX AT 6 WEEKS 1,4,9 = Molecular Weight Marker
2 = SNAP-25 Control
3 = Fresh Type A complex Cleavage
5 = 5°C Buffer
6 = 5°C α-CD
7 = 25°C Buffer
8 = 25°C α-CD

STABILIZATION OF *CLOSTRIDIUM BOTULINUM* NEUROTOXIN COMPLEX

This application claims the benefit of provisional application No. 60/720,854 filed Sep. 26, 2005, the entire content of which is expressly incorporated herein by reference thereto.

BACKGROUND OF THE INVENTION

1. Field of the Invention

The present invention relates to a pharmaceutical composition comprising *Clostridium botulinum* neurotoxin and to a method of stabilizing the same. Particularly, the present invention is directed to a stabilized pharmaceutical composition including *C. botulinum* Type A and a cyclodextrin.

2. Description of Related Art

*Botulinum* neurotoxins are produced from anaerobic *bacillus Clostridium botulinum*. Seven related protein neurotoxins, known as serotypes A through G, are produced by different strains of the *bacillus*. Each of the seven serotypes of the *botulinum* neurotoxins is a large protein having a molecular weight of about 150 kDa, and a 100 kDa heavy chain of amino acid residues and a 50 kDa light chain of amino acid residues coupled by at least one disulfide linkage.

*Clostridium botulinum* neurotoxins, which cause the disease of botulism by blocking the release of the neurotransmitter, acetylcholine at the neuromuscular junction, are the most toxic proteins currently known to mankind. Food-borne botulism results from the consumption of improperly stored foods in which anaerobic *C. botulinum* grows and releases the toxin. In other forms of botulism, *C. botulinum* also produces the neurotoxin resulting in toxigenesis. For example, wound botulism results when the spores of *C. botulinum* are introduced into an open skin abrasion. The colonization of the wound is followed by the release of *botulinum* toxin. Similarly, infant botulism results from the consumption of *C. botulinum* spores followed by colonization in the intestine and toxigenesis.

Although the *botulinum* neurotoxins are known to be the most lethal natural toxin known to man, these lethal poisons have become utilized in the medical community as drugs with many indications. In this regard, the *botulinum* neurotoxins have been used to treat strabismus, and local injections of *botulinum* neurotoxin are now considered a safe and efficacious treatment for many neurological and non-neurological conditions. Recently, it has been observed that *botulinum* neurotoxin is useful as a treatment for diseases of the gastrointestinal tract. *Botulinum* neurotoxin is not only potent in blocking skeletal neuromuscular transmission, but also block cholinergic nerve endings in the autonomic nervous system. The capability to inhibit contraction of smooth muscles of the gastrointestinal tract was first suggested based on in vitro observations and later demonstrated in vivo, it has also been shown that *botulinum* neurotoxin does not block non adrenergic non cholinergic responses mediated by nitric oxide. This has further promoted the interest to use *botulinum* neurotoxin as a treatment for overactive smooth muscles and sphincters, such as the lower esophageal sphincter to treat esophageal achalasia, or the internal anal sphincter to treat anal fissure.

Commercially available pharmaceutical compositions comprising *botulinum* toxin are marketed under the trademarks including BOTOX® (Allergan, Inc. Irvine Calif.), Dysport® (Ipsen Ltd. Berkshire, U.K.) and Myobloc® (Elan Corp. Dublin Ireland). Typically, the pharmaceutical compositions are sold as vacuum-dried form that must be reconstituted with a diluent prior to actual usage. One major drawback to using the commercially available botulinum toxin preparations is the very short shelf life of the composition. In this regard, the actual usage of the pharmaceutical composition should be administered within about four hours after reconstitution because the *botulinum* toxin is very susceptible to denaturation due to surface denaturaion, heat, and alkaline conditions.

The susceptible denaturation of the *botulinum* neurotoxin reconsitution necessiates a need for methods of preserving the *botulinum* neurotoxin. It has been found that the *Clostridium botulinum* bacteria secretes the neurotoxin along with a group of neurotoxin associated proteins ("NAPs"). Research has shown that not only do the NAPs have a critical role in the toxico-infection of the *botulinum* neurotoxins, but the NAPs have an important role in the toxicity of the *botulinum* neurotoxin. In particular, it has been demonstrated the oral toxicity of the neurotoxin type A decreases by 43,000-fold upon removal of the NAPs. It has also been shown that the NAPs act to protect the neurotoxin against various environmental conditions including exposure to proteases, acidity, and heat. See, Kitamura, M., Sakaguchi, S., and Sakaguchi, G. (1969) Significance of the 12S toxin of *Clostridium botulinum* type E. *Bacteriol.* 98, 1173-1178; Sugii, S., Ohishi, I., and Sakagch, G., (1977) Botulogenic properties of vegetables with special reference to molecular size of the toxin in them, *J. Food Safety* 1, 53-65. Accordingly, it has been suggested that the NAPs interact with the neurotoxin to protect it from adverse environmental conditions. This protective role has led to the hypothesis that NAPs are important for the preservation of the structural integrity of the neurotoxin, as well as preservation of its activity.

Cyclodextrins are cyclic multiclyclopyranose unites connected by alpha-(1-4) linkages. The most widely known cyclodextrins are A, B, G-cyclodextrins, and their derivatives. The cyclic nature of the cyclodextrins, the hydrophobic properties of their cavities and the hydrophilic properties of their outer surfaces enable them to interact with other chemicals and produce inclusion compounds which are characterized by improved solubilities and stabilities. For example, U.S. Pat. No. 6,818,662 to Ito et al. discloses that solfobutyl ether B-cyclodextrin increases the solubility and light stability of N-(3-chloro-4-morpholin-4-yl)phenyl-N'-hydroxyimodoformadinie.

Although cyclodextrins are known to form inclusion complexes with drugs, there has been no disclosure or suggestion that a cyclodextrin can stabilize a *botulinum* neurotoxin. In fact, it has been thought that cyclic polymers including cyclodextrins can not be used to preserve or stabilize a *botulinum* neurotoxin. See, U.S. Patent Application Publication 2003/0118598 to Hunt, in which it has been taught that the *botulinum* neurotoxin can not utilize the cyclodextrin cavity because the cavity is much smaller in size than the neurotoxin. Accordingly, cyclodextrins cannot form inclusion complexes with *botulinum* neurotoxin.

There remains a need for an efficient and economic method and system for preparing a pharmaceutical composition comprising *botulinum* neurotoxin and a method for stabilizing and preserving the *botulinum* neurotoxin. The present invention satisfies these needs.

SUMMARY OF THE INVENTION

The purpose and advantages of the present invention will be set forth in and apparent from the description that follows, as well as will be learned by practice of the invention. Additional advantages of the invention will be realized and attained by the methods and compositions particularly pointed out in the written description and claims hereof, as well as from the appended drawings.

The present invention seeks to alleviate the problems associated with rapid degradation or denaturation of *botulinum* neurotoxin by providing a novel composition that exhibits improved stability properties. In particular, the present invention seeks to provide a method for producing a *botulinum* neurotoxin composition with improved stability properties in an efficient and economically advantageous manner.

To achieve these and other advantages and in accordance with the purpose of the invention as described herein, the invention includes novel inclusion complexes of *botulinum* neurotoxin which exhibit improved stability properties. The invention also includes method for stabilizing *botulinum* neurotoxin. The neurotoxin is preferably stabilized by forming a cyclodextrin inclusion complex.

In accordance with the invention, a composition is provided which comprises a *botulinum* neurotoxin and a cyclodextrin or a derivative thereof. The *botulinum* neurotoxin can be pure or purified and can be Type A, B, C, D, E, F, or G. Preferably, the *botulinum* neurotoxin is Type A. The cyclodextrin can be alpha, beta, or gamma cyclodextrin. Alternatively, the cyclodextrin can be a cyclodextrin derivative, such as but not limited to hydroxyalkyl, carboxamide, diethylaminoethyl, carboxymethyl or dihydroxyalkyl derivative of α cyclodextrin, β-cyclodextrin, or γ-cyclodextrin.

Advantageously, the cyclodextrin is present in an amount sufficient to form a complex with the *botulinum* neurotoxin to provide a stabilized *botulinum* neurotoxin. Ordinarily, as known in the art, the *botulinum* neurotoxin is very susceptible to degradation or denaturation. Typically, commercially available *botulinum* neurotoxins, such as BOTOX®, DYSPORT®, and MYOBLOC®, lose their potency in about 4 hours. It has been surprisingly found that the formation of the cyclodextrin-*botulinum* neurotoxin complex preserves the potency of the *botulinum* neurotoxin for at least about 23 weeks.

In one embodiment, the pharmaceutical composition comprises *botulinum* neurotoxin Type A and alpha-cyclodextrin. Only about 4% of the *botulinum* neurotoxin degrades over a 23-week period when at 4 C, whereas about 52 to 48% of the neurotoxin degrades over a 23-week period at 25 C.

In another embodiment, the composition comprises *botulinum* neurotoxin Type A and a beta-cyclodextrin. Less than 7% of the *botulinum* neurotoxin at 4 C degrades over a 23-week period, while less than 65% of the *botulinum* neurotoxin at 25 C degrades over the same time period.

In yet another embodiment, the composition comprises *botulinum* neurotoxin Type A and gamma-cyclodextrin. In this embodiment, the degradation of the neurotoxin at 4 C was less than 2%, and the degradation of the neurotoxin at 25 C was less than 55%, both over a 23-week period. Accordingly, the composition has an increased stability over time.

In one preferred embodiment, the *botulinum* neurotoxin inclusion complex of the invention is admixed with a pharmaceutically acceptable diluent, carrier or excipient (including combinations thereof) to form a pharmaceutical composition. The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable carriers include lactose, starch, glucose, methyl cellulose, magnesium stearate, mannitol, sorbitol and the like. Examples of suitable diluents include ethanol, glycerol and water. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The composition in accordance with the invention may be, for example and not limitation, in the form of an injectable solution, a vacuum dried preparation, or a freeze-dried preparation. also include.

In accordance with another aspect of the invention, a method is provided for increasing the stability of *botulinum* neurotoxin comprising subjecting the *botulinum* neurotoxin to cyclodextrin to form an inclusion complex. Preferably, the molar ratio of the cyclodextrin to *botulinum* neurotoxin is at least 25:1 to 50:1, and most preferably 39:1. As used herein, the term "cyclodextrin" refers to a compound having a plurality of cyclopyranose units and include alpha, beta, gamma-cyclodextrins, any derivative or salt thereof and any combination thereof. The method of the invention provides a cyclodextrin-*botulinum* neurotoxin inclusion complex having markedly improved stability. Consequently, this improved stability serves to provide a *botulinum* neurotoxin with increased shelf-life. Preferably, the *botulinum* neurotoxin is subjected to the cyclodextrin in an aqueous system. The aqueous system has a pH of about 6.8 to 7.6 and can contain between 3 and 25 mM cyclodextrin, between 5 and 25 nM phosphate buffer. Most preferably, the aqueous system comprises 10 mM cyclodextrin, 10 mM sodium phosphate buffer, and has a pH 7.4.

In one particularly preferred embodiment of the invention, the aqueous solution of the cyclodextrin inclusion product of *botulinum* neurotoxin in accordance with the invention can be used in a variety of forms. For example, the complex may be prepared as an injectable drug or can be dried to form a reconstitutable powder, as known in the art.

It is to be understood that both the foregoing general description and the following detailed description are exemplary and are intended to provide further explanation of the invention claimed.

The accompanying drawing, which is incorporated in and constitutes part of this specification, is included to illustrate and provide a further understanding of the method and system of the invention. Together with the description, the drawings serve to explain the principles of the invention.

DETAILED DESCRIPTION OF THE PREFERRED EMBODIMENT

Reference will now be made in detail to the present preferred embodiments of the invention, an example of which is illustrated in the accompanying drawing. The method and corresponding steps of the invention will be described in conjunction with the detailed description of the system.

The methods and compositions presented herein may be used for alleviating the problems associated with instability of *botulinum* neurotoxin. The present invention is particularly suited for providing a novel inclusion complex of *botulinum* neurotoxin which exhibits improved stability, and method of making the inclusion complex. For purpose of explanation and illustration, and not limitation, an exemplary embodiment of the system in accordance with the invention is shown in drawing FIGS. 1 to 11 inclusive.

Specifically, and in accordance with the present invention, composition comprises a *botulinum* neurotoxin and cyclodextrin. The *botulinum* neurotoxin and the cyclodextrin form an inclusion complex which exhibits markedly improved stability. The *botulinum* neurotoxin embodied herein includes Types A, B, C, D, E, F, and G. In the preferred embodiment, the *botulinum* neurotoxin is Type A. The cyclodextrin embodied herein includes alpha, beta, and gamma-cyclodextrin, and any derivative or salt thereof.

In accordance, with another embodiment of the invention, a method for stabilizing *botulinum* neurotoxin is provided. The method includes subjecting the *botulinum* neurotoxin to cyclodextrin to form a stable inclusion complex.

Comparative Studies

A series of studies were performed on the stability and preservation of the *botulinum* neurotoxin Type A and cyclodextrin complex ("TANC/CD"). In the series of studies, the Type A neurotoxin from the *bacillus Clostridium botulinum* ("TANC") was incubated for 23-weeks with a each of the alpha, beta, and gamma cyclodextrins and analyzed by HPLC-Gel filtration ("HPLC-GF") methods, as known in the art.

Figure 1:
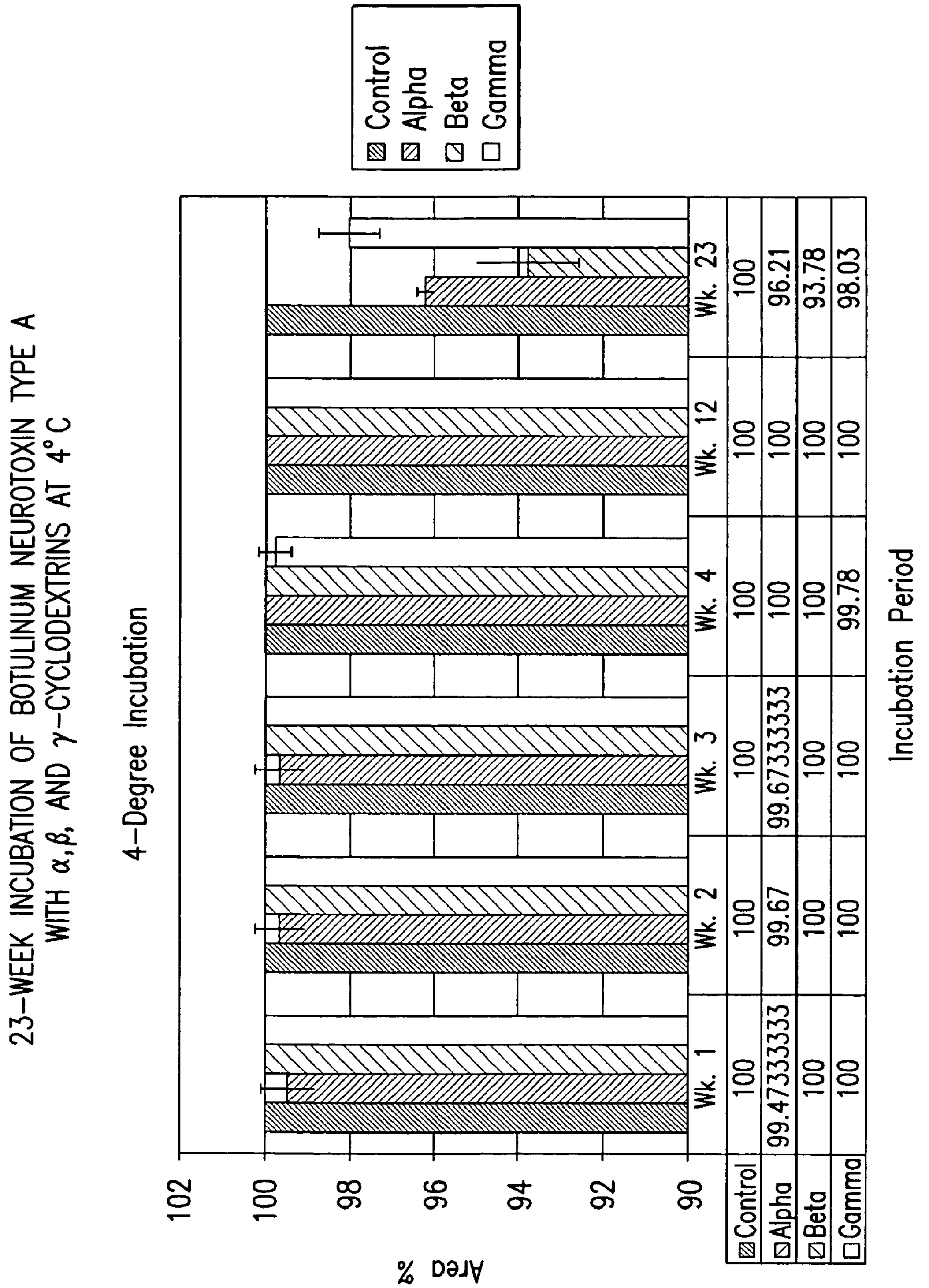
FIG. 1 is a bar graph illustrating the results of a 23-week study of the incubation of neurotoxin Type A complex with alpha, beta, and gamma cyclodextrins at 4° C. in accordance with the invention.

As depicted in FIG. 1, the results of the 23-week TANC/CD study illustrates the total peak area determined to be non-degraded TANC at 4° C. As used herein the term "total peak area" refers to the amount of protein represented by the elution time peak. A reduction in the total peak area would reflect reduction in the amount of protein at that peak, suggesting degradation or dissociation into smaller fragments or components of the complex. As shown, the total peak area of the control is 100% throughout the 23-week period. Accordingly, the control has undergone no degradation of the TANC over the 23-week period of time. The control used in this study comprised 10 mM cyclodextrin and 10 mM sodium phosphate buffer at pH 7.4.

FIG. 1 depicts that each of the alpha, beta, and gamma-cyclodextrin incubated TANC have peaks which indicate at least a small amount of degradation. As illustrated, the gamma-cyclodextrin incubated TANC shows the least degradation of about 2% at 4° C. The beta-cyclodextrin incubated TANC has the most degradation (as compared to the other cyclodextrins) of more than 6%. The small amount of degradation of the gamma-cyclodextrin incubated TANC sample is most likely a result of the denaturation of a small amount of the complex structure.

Figure 5:
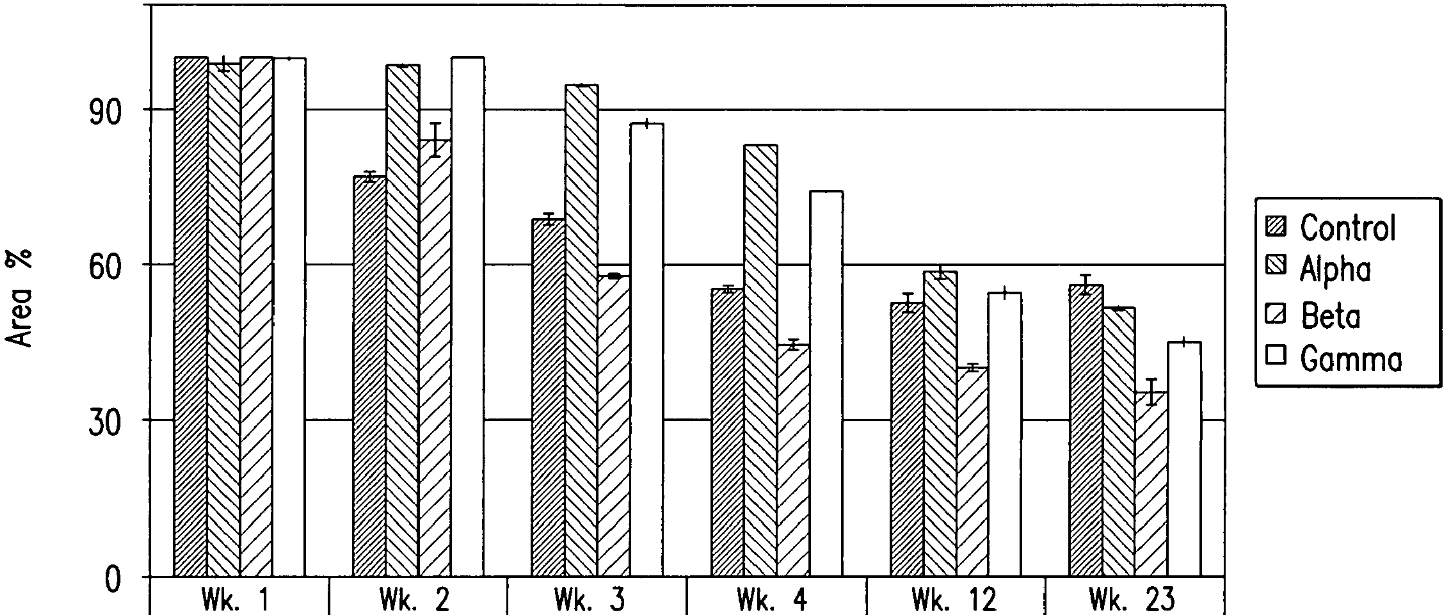
FIG. 5 is bar graph illustrating the results of a 23-week study of the incubation of neurotoxin Type A complex with alpha, beta, and gamma cyclodextrins at room temperature in accordance with the invention.
Figure 6:
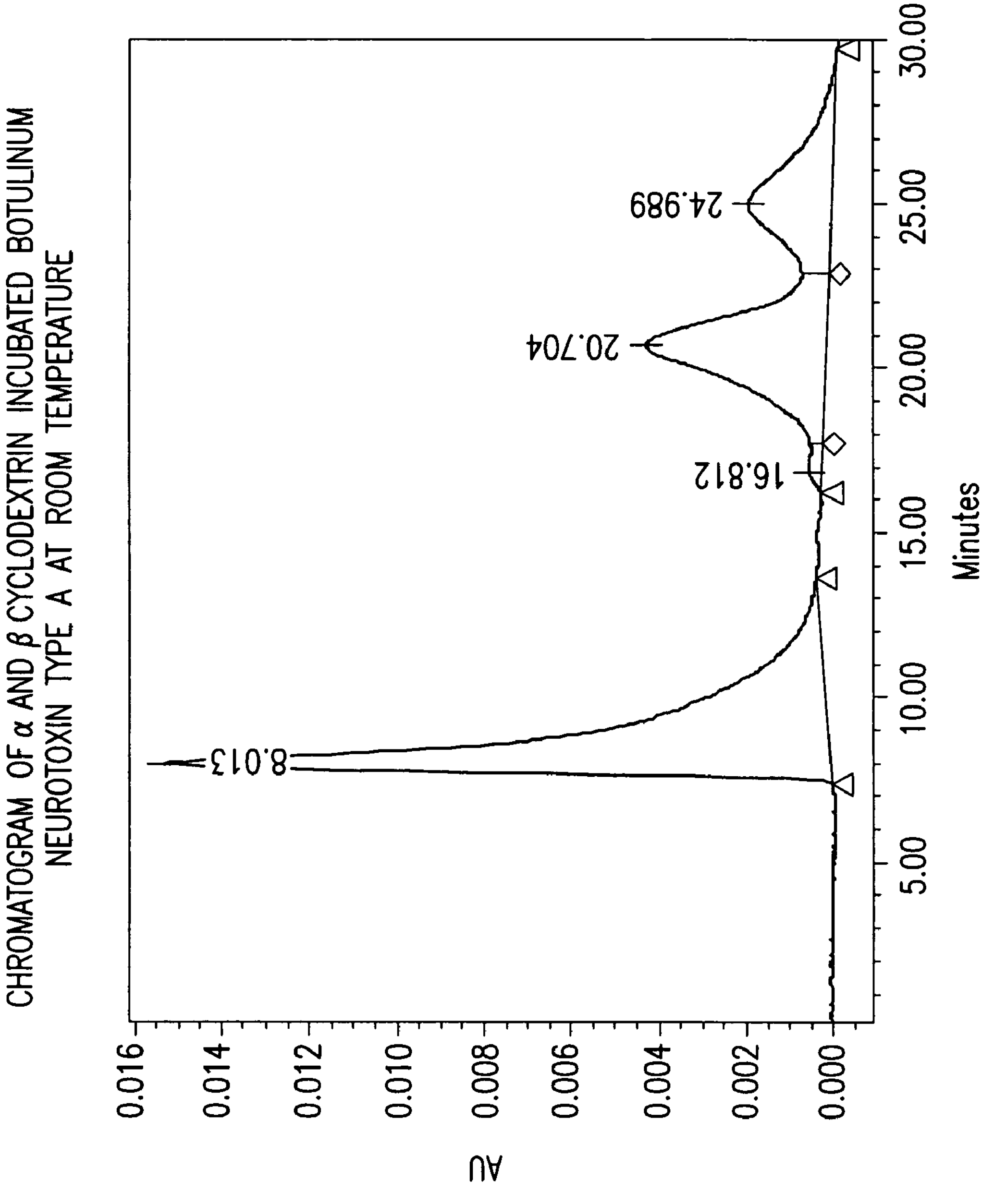
FIGS. 6, 6*a*, 6*b* and 6*c* are chromatograms illustrating the spectra from the neurotoxin Type A control at room temperature in accordance with the invention.
Figures 6A, 6B, 6C:
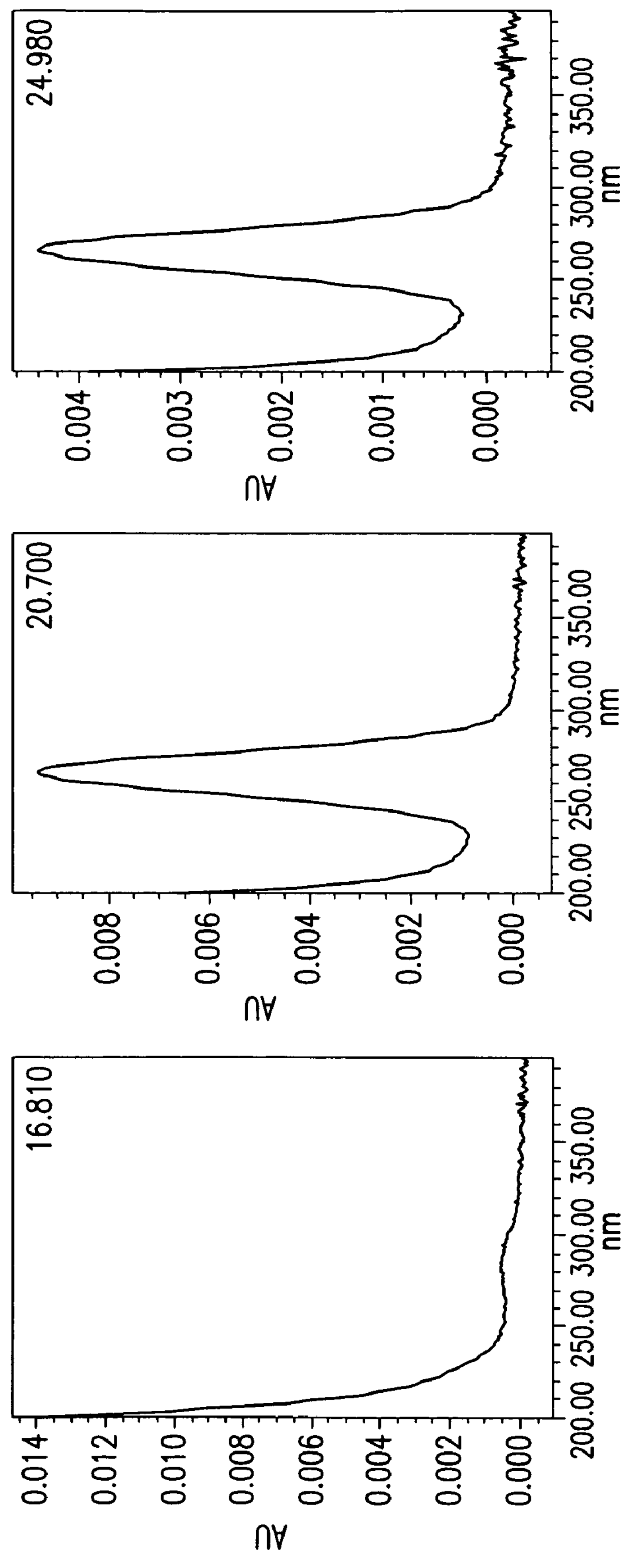
Figure 7:
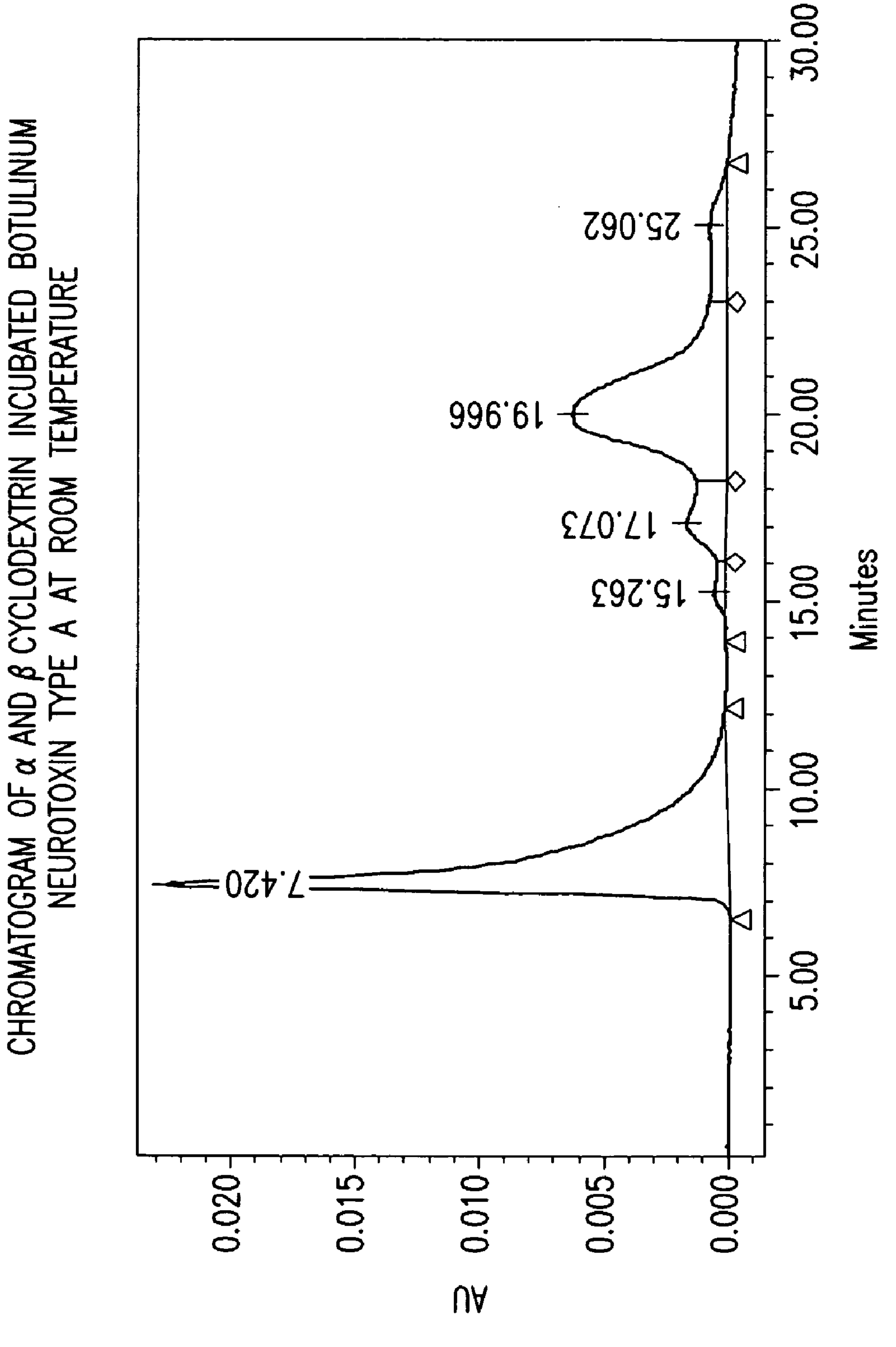
FIGS. 7, 7*a*, 7*b*, 7*c* and 7*d* are chromatograms illustrating the spectra from the alpha-cyclodextrin incubated neurotoxin Type A at room temperature in accordance with the invention.
Figure 7A:
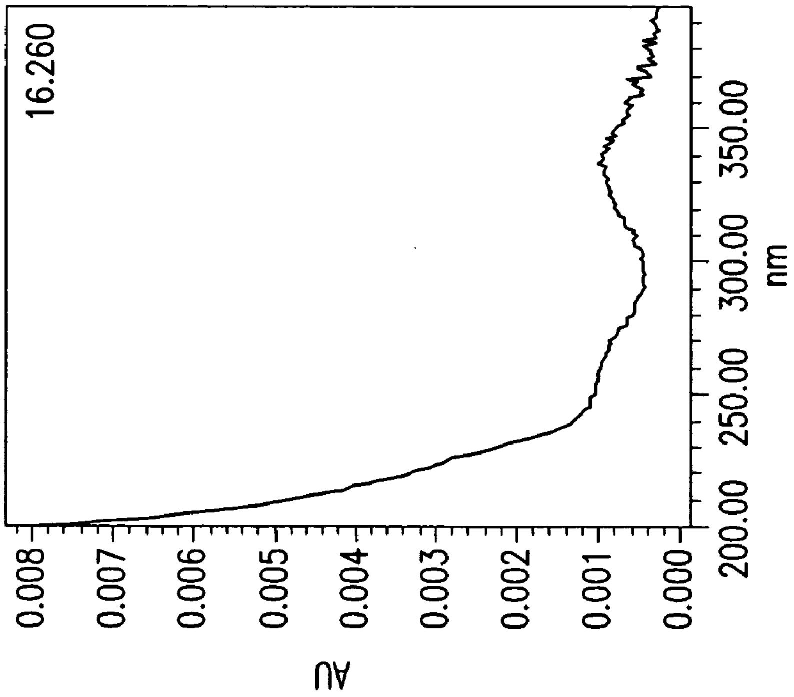
Figure 7B:
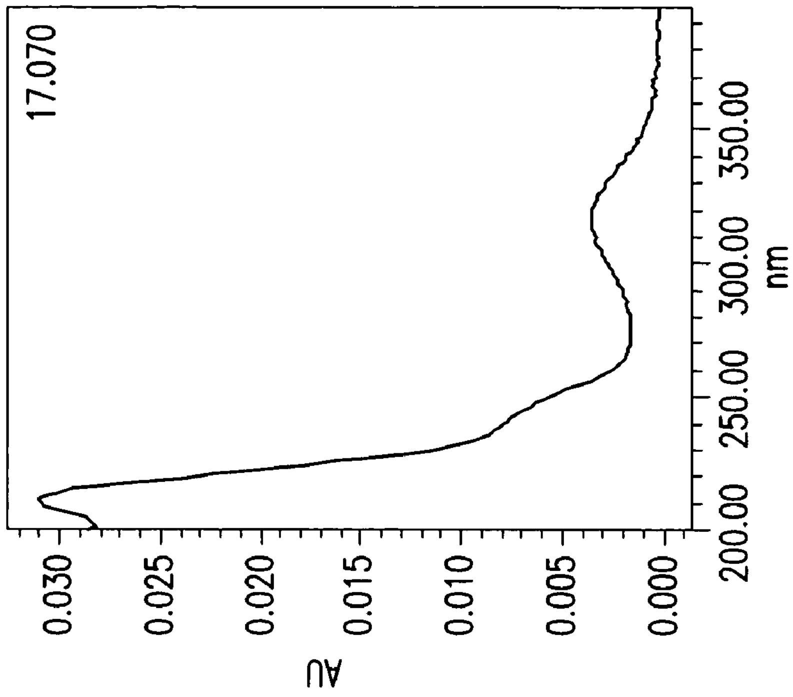
Figure 7D:
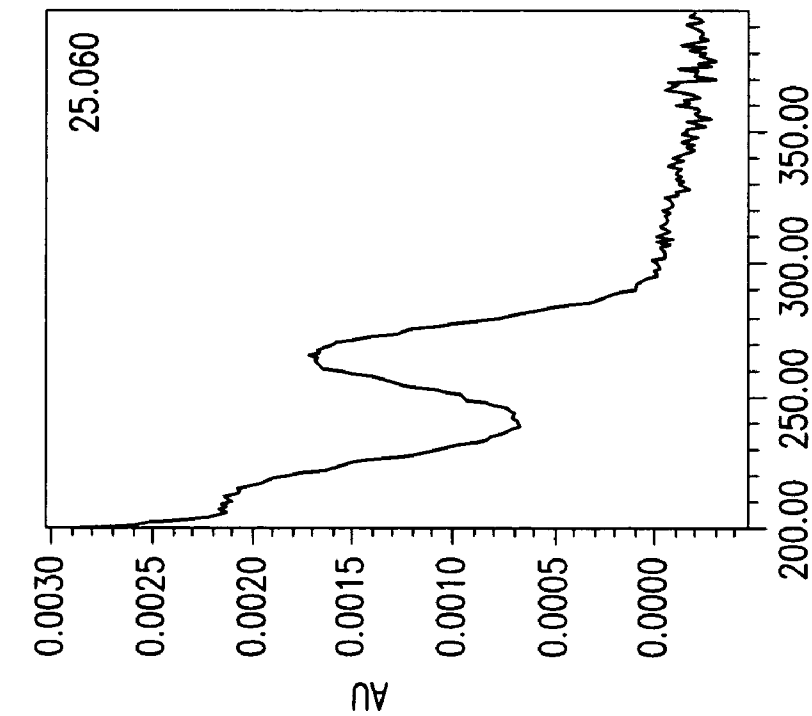
Figure 7C:
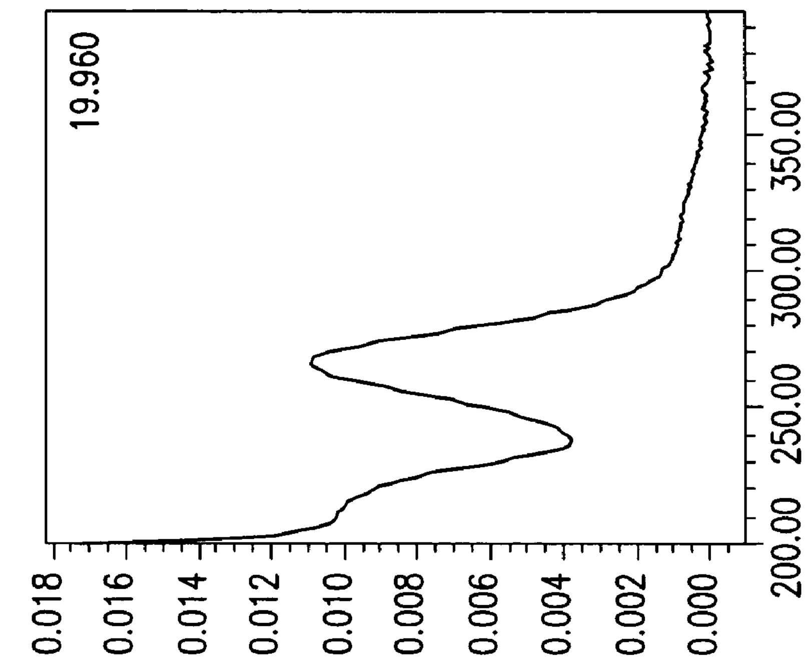

As shown and depicted in FIG. 5, further control of the stabilization effect of the 10 mM sodium phosphate buffer was observed at room temperature (25° C.), and which depicts degradation of the complex by about 42%.

Figure 2:
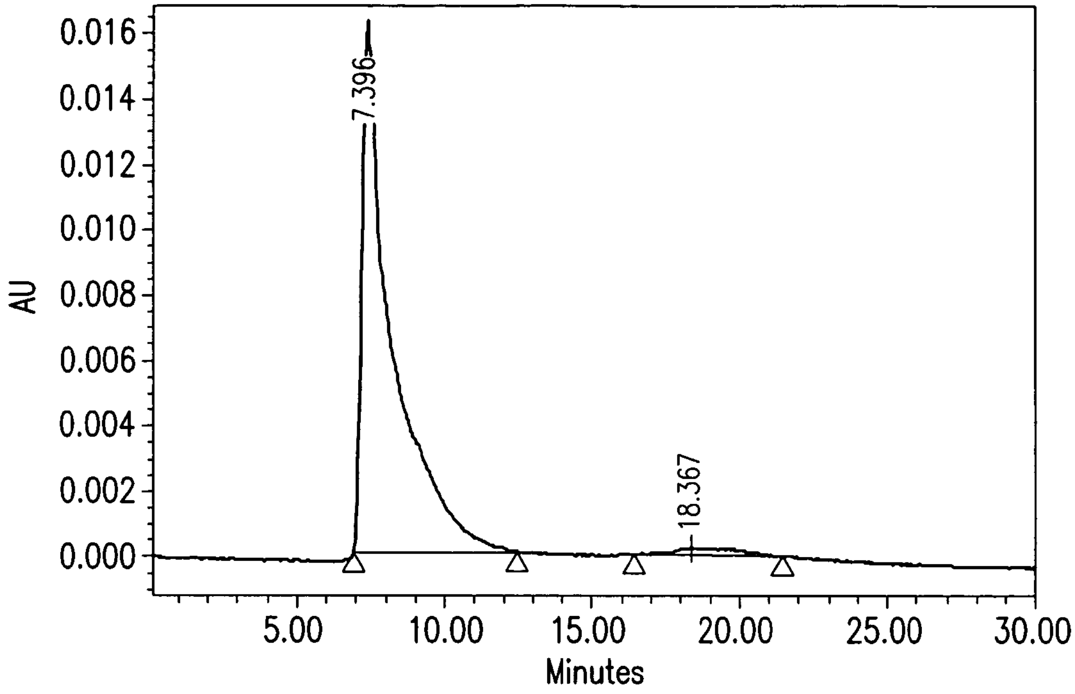
FIGS. 2 and 2*a* are chromatograms illustrating the spectra from the gamma-cyclodextrin incubated neurotoxin Type A at 4° C. in accordance with the invention.
Figure 2A:
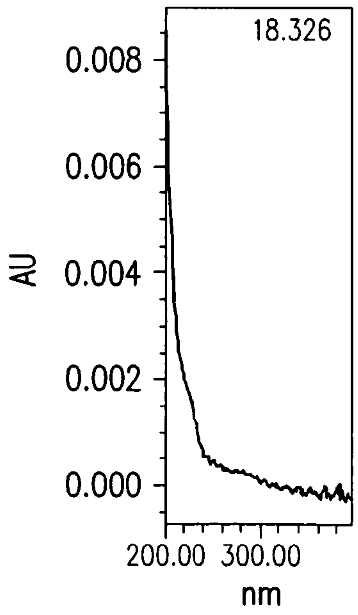

The chromatogram extracted at 280 nm as depicted in FIG. 2 indicates that the TANC peak has a relatively stable retention time of about 7.4 minutes. The degradation peak, however, has a retention time of about 18.3 minutes. Thus, smaller protein fragments or components are retained for a longer period of time in a gel filtration column. The longer retention time refers to the proteins of smaller size, which may be produced either by degradation of the complex or dissociation of its components. Further, as depicted in FIG. 2*a*, a 200 nm to 400 nm wavelength scan extracted from the gamma-incubated TANC sample chromatogram indicates that the 18.3 minute peak has a λ max value at about 225 and 280 nm thereby indicating the presence of protein. Accordingly, the degradation of the gamma-cyclodextrin incubated TANC is a disruption of the complex structure and not a degradation of the cyclodextrin complex surrounding the TANC.

Figure 3:
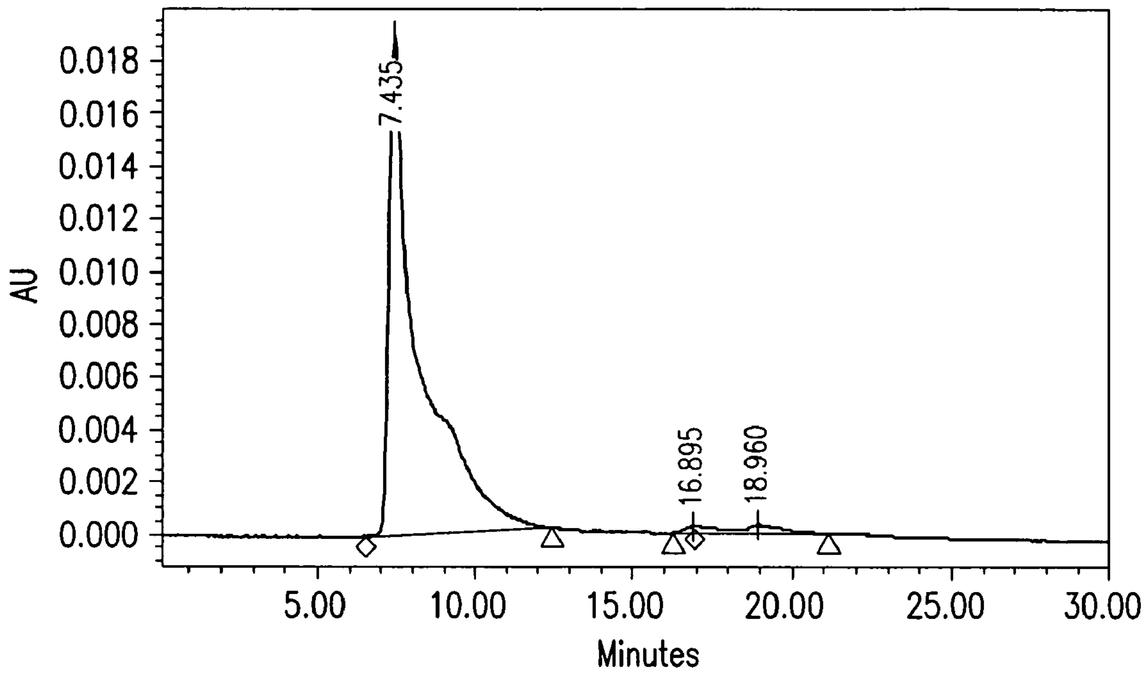
FIGS. 3, 3*a* and 3*b* are chromatograms illustrating the spectra from the alpha-cyclodextrin incubated neurotoxin Type A at 4° C. in accordance with the invention.
Figure 3A:
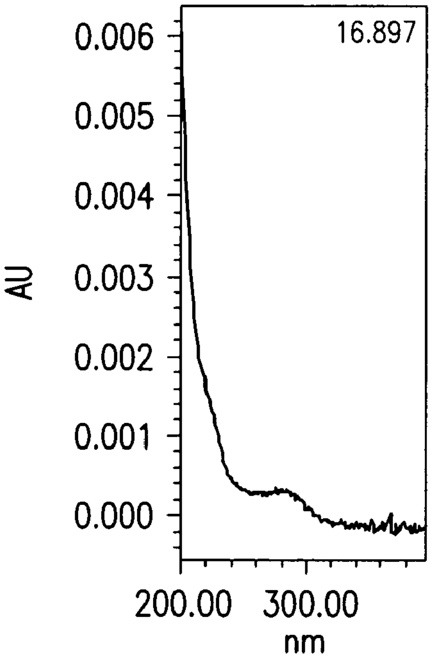

Each of the alpha- and beta-cyclodextrin incubated TANC samples revealed two degradation peaks. Extracted spectra from the first of the degradation peaks for the alpha and beta cyclodextrin incubated TANC samples displaced results similar to that of the gamma-cyclodextrin peaks, as illustrated in FIGS. 3*a* and 4*a*, respectively. Specifically, as depicted in FIG. 3*a*, a 200*nm* to 400 nm wavelength scan extracted from the alpha-cyclodextrin incubated TANC sample indicates that the 16.9 minute peak has λ max values at about 280 nm thereby indicating the presence of protein. Additionally, and as depicted in FIG. 4*a*, a 200 nm to 400 nm wavelength scan extracted from the beta-cyclodextrin incubated TANC sample indicates that the 17.4 minute peak has λ max values at about 280 nm thereby indicating the presence of protein. Further, the spectra depicted in FIG. 4*a* also indicates a λ max value at about 265 nm, thereby indicating that the beta-cyclodextrin is no longer in complex with the TANC.

Figure 3B:
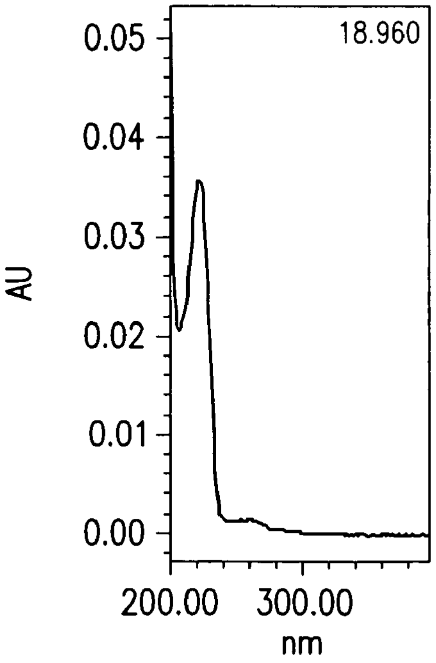
Figure 4:
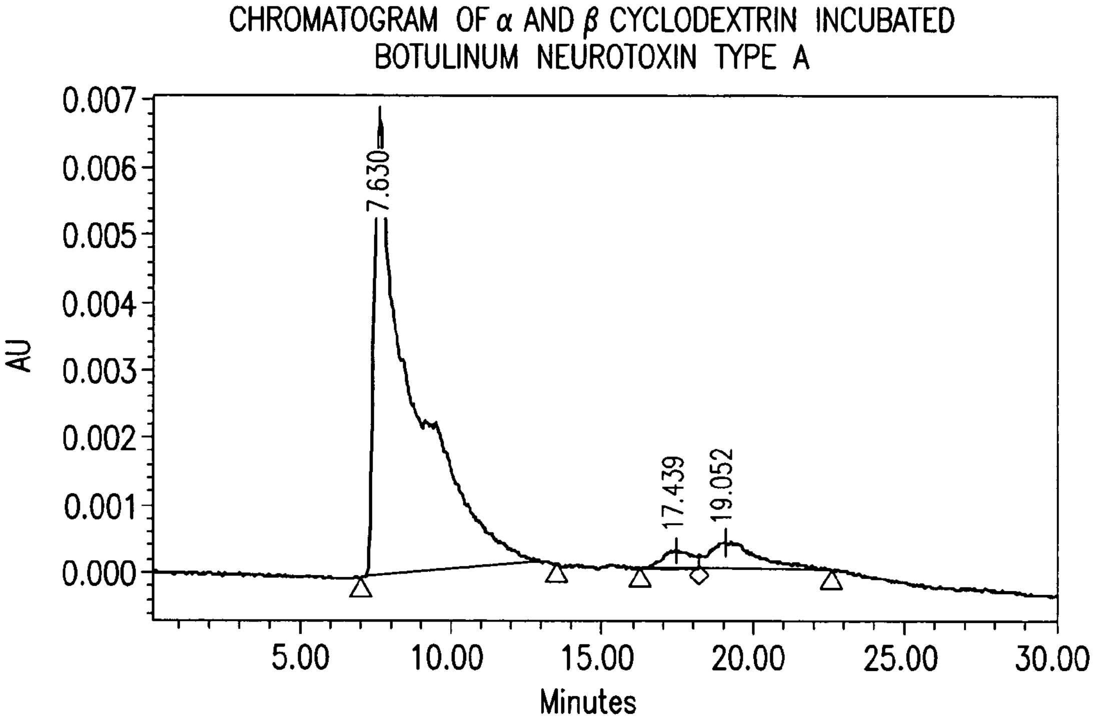
FIGS. 4, 4*a* and 4*b* are chromatograms illustrating the spectra from the beta-cyclodextrin incubated neurotoxin Type A at 4° C. in accordance with the invention.
Figure 4A:
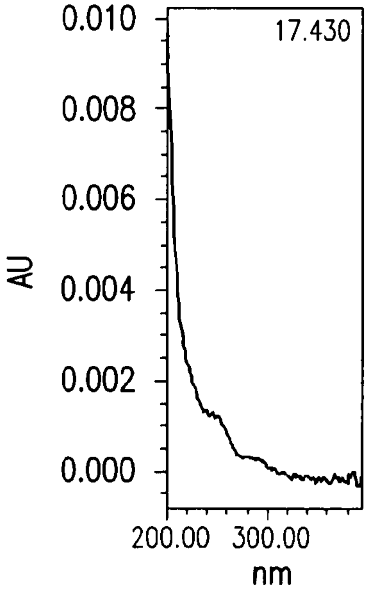
Figure 4B:
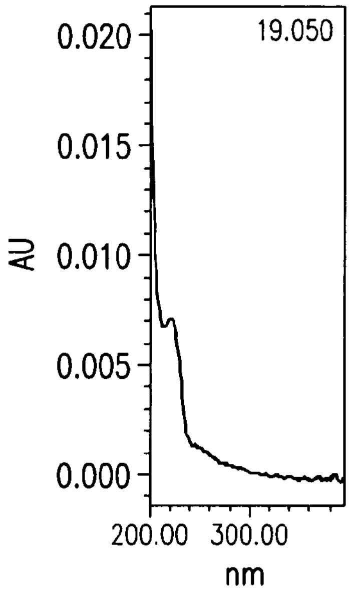

The second of the degradation peaks for the alpha-cyclodextrin incubated TANC and the beta-cyclodextrin incubated TANC, as illustrated in FIGS. 3*b* and 4*b*, respectively, are characteristic of uncomplexed cyclodextrins. The spectra illustrated in FIGS. 3*b* and 4*b* each have λ max values at about 225 nm and at about 265 nm.

As can be seen from FIGS. 3 and 4, the 7.4 minutes peak for the alpha-cyclodextrin TANC complex and the 7.6 minute peak for the beta-cyclodextrin TANC each have a distinctive shoulder at about 9 minutes. An extracted spectra for each of these shoulders illustrated that each shoulder yielded a peak representative of TANC itself. This data indicates that a large portion of the TANC complex (alpha- at about 22%; beta at about 31% by absorbance) which will break away from the TANC/CD complex.

As depicted in FIG. 5 and embodied herein, the results of the 23-week TANC/CD study illustrates the total peak area determined to be non-degraded TANC at room temperature. As shown, each of the cyclodextrin TANC samples including the control indicate greater amounts of degradation than comparable samples incubated at 4° C. As with the 4° C. incubation results, the room temperature control sample had the lowest degree of TANC degradation of about 44% degradation over the 23 week period. FIG. 5 also shows that the alpha-cyclodextrin incubated TANC sample, as compared to the beta- and gamma-cylcodextrin incubated TANC complexes, had the least degradation over the 23-week period. The degradation of the alpha-cyclodextrin TANC was about 52 to 48%, whereas, the beta-cyclodextrin incubated TANC had a 65% degradation, and the gamma-cyclodextrin incubated TANC had a 55% degradation.

As depicted in FIG. 5 the total peak area of the control at room temperature is 100% in week 1. However, the control shows some degradation in week 2 of about 23% and continually degrades over the 23 week period to about 44% degradation in week 23. The other cyclodextrin incubated TANC had greater degrees of TANC degradation. Specifically, the beta-cyclodextrin incubated TANC at room temperature degraded by about 65%, and the gamma-cyclodextrin incubated TANC at room temperature degraded by about 55% over the 23-week period. The alpha-cyclodextrin incubated TANC at room temperature had less degradation (about 52 to 48%) than either the beta and gamma-cyclodextrin incubated TANC.

Figure 8:
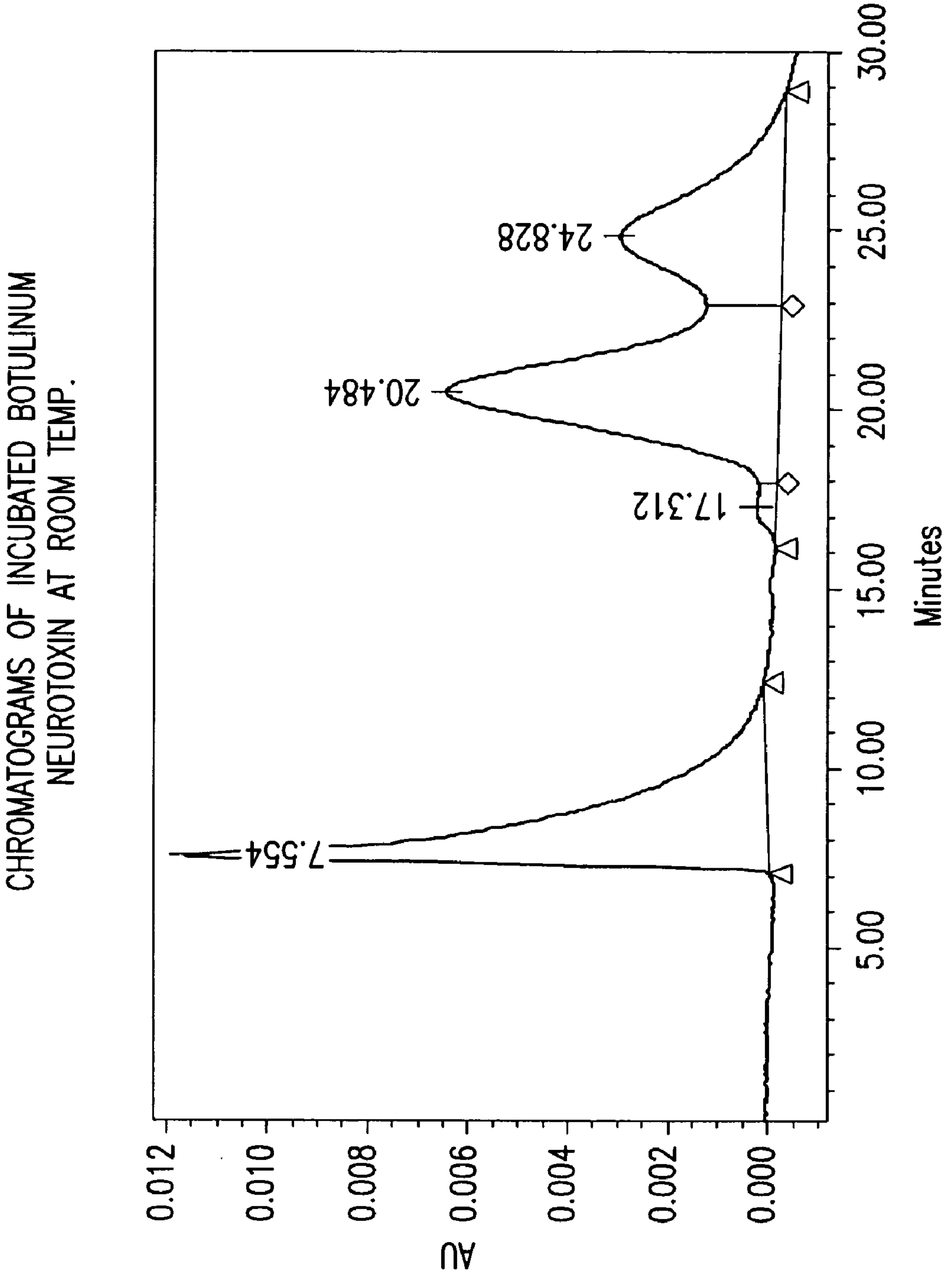
FIGS. 8, 8*a*, 8*b*, and 8*c* are chromatograms illustrating the spectra from the beta-cyclodextrin incubated neurotoxin Type A at room temperature in accordance with the invention.
Figure 8C:
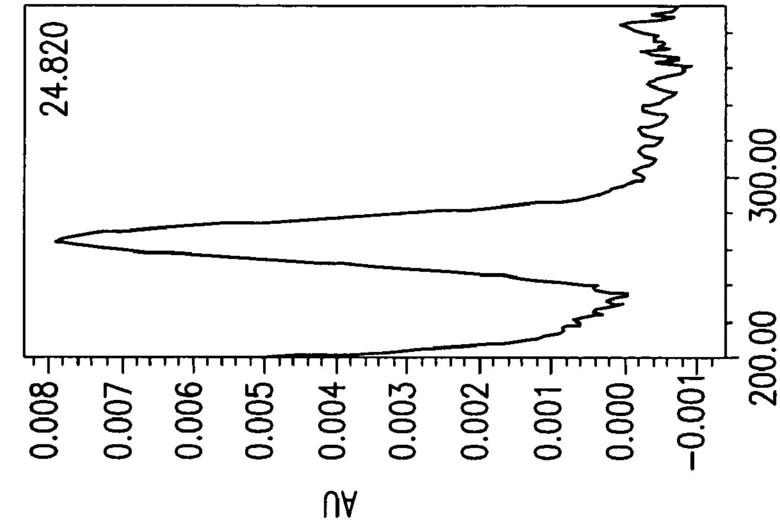
Figure 8B:
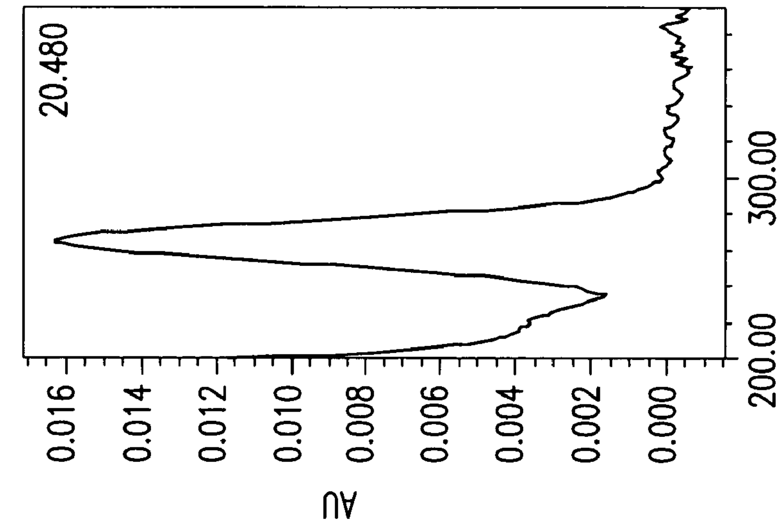
Figure 8A:
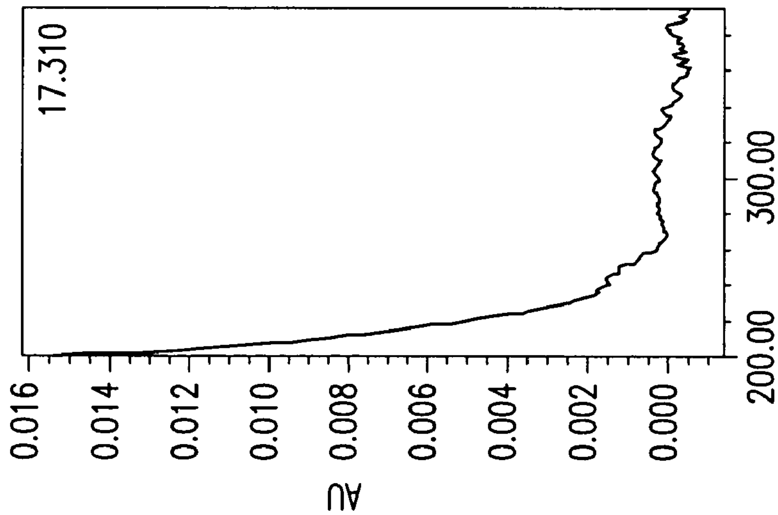
Figure 9:
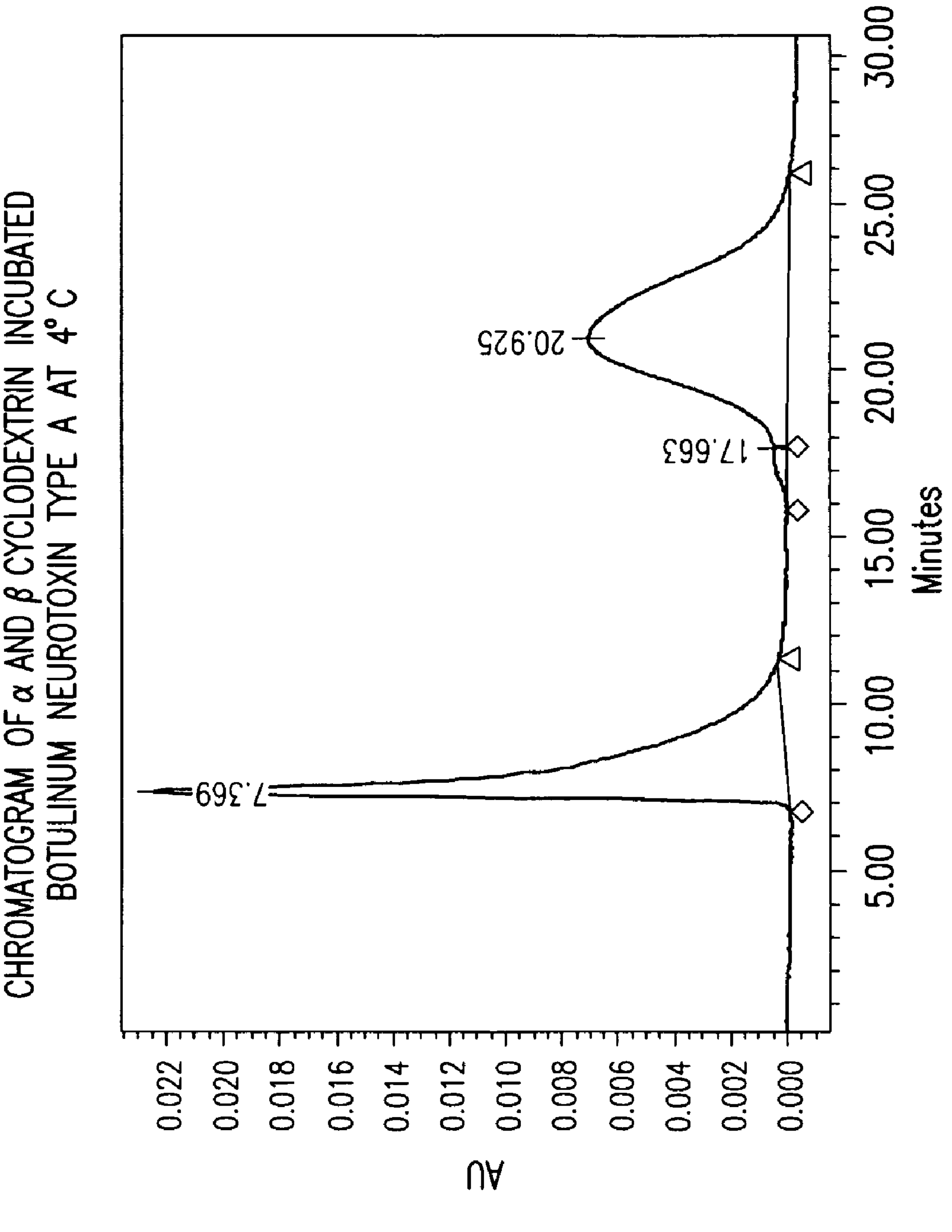
FIGS. 9, 9*a* and 9*b* are chromatograms illustrating the spectra from the gamma-cyclodextrin incubated neurotoxin Type A at room temperature in accordance with the invention.
Figure 9A:
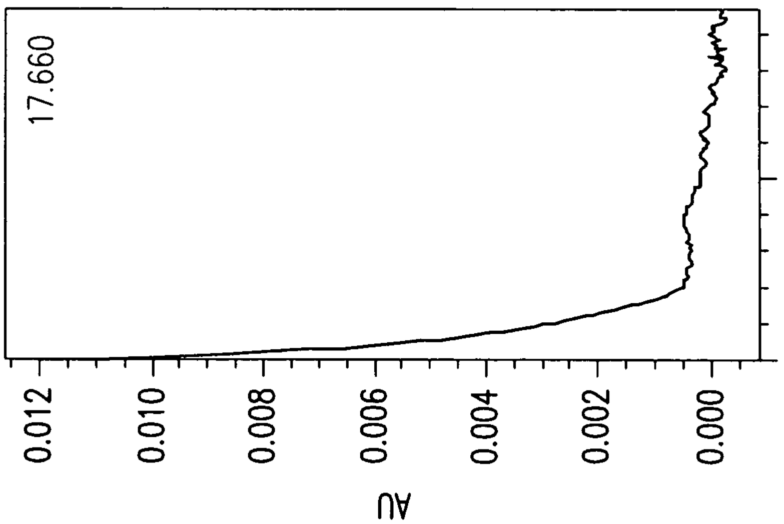
Figure 9B:
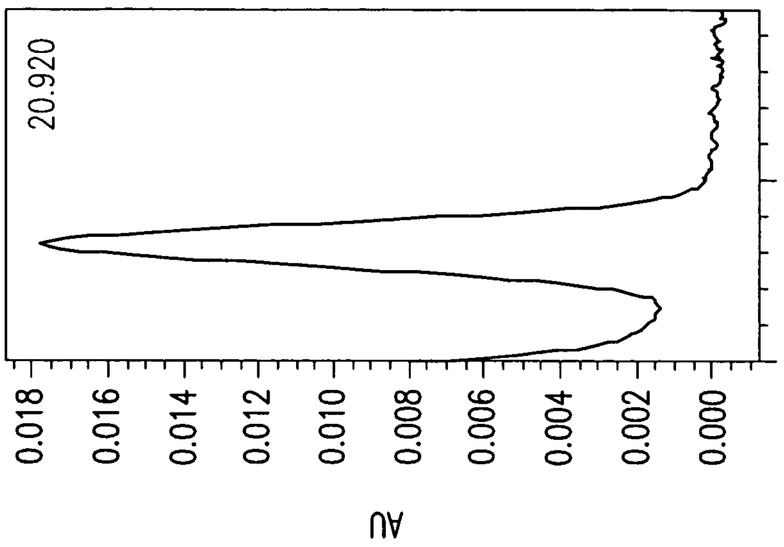

FIGS. 6, 6*a*, 6*b*, and 6*c* each show chromatograms and extracted spectra of the control cyclodextrin incubated TANC at room temperature. FIGS. 7, 7*a*, 7*b*, and 7*c* each show chromatograms and extracted spectra of the alpha-cyclodextrin incubated TANC at room temperature, FIGS. 8, 8*a*, 8*b*, and 8*c* each illustrate the chromatogram and extracted spectra of the beta-cyclodextrin incubated TANC at room temperature, and FIGS. 9, 9*a*, and 9*b* each illustrate the chromatogram and extracted spectra of the gamma-cyclodextrin incubated TANC at room temperature. In each chromatogram, the wavelength scans of the peaks, which represent the degradation products for each of the cyclodextrin incubated TANC complexes are similar to that of the cyclodextrin incubated TANC complexes at 4° C., as illustrated in FIG. 2 through and including 4*b*. The wavelength scans represented in FIGS. 6 through 9 indicate either denaturation of the protein complex, cyclodextrin complex, or both. The early degradation peaks in FIGS. 7*a*, 7*b*, and 8*a*, at about 15.3 min., 17.1 min., and 17.3 min., respectively, each depicted max values slightly above 300 nm.

Degradation Product Molecular Mass

An attempt was made to determine the molecular mass of the degradation products using the standard curve (y=−1.667x+7.409) generated for this column. The elution time for the Blue Dextrin (5.115 min.) served as the void volume ($V_{ot}$) for the $R_f$ calculations ($V_{et}/V_{ot}$). Tables 1 and 2, below, each show the values from the calculations.

TABLE 1

| 4° C. degradation product molecular masses | | |
|---|---|---|
| Sample | Peak 1, RT/MW (min/Da) | Peak 2, RT/MW (min/Da) |
| Control | — | — |
| α-CD | 16.895/80.0* | 18.960/17.0* |
| β-CD | 17.439/53.1* | 19.052/15.8* |
| γ-CD | 18.367/27.8* | — |

*indicates values below the linear range of the GF column.

TABLE 2

| Room temperature degradation product molecular masses | | | | |
|---|---|---|---|---|
| Sample | Peak 1, RT/MW (min/Da) | Peak 2, RT/MW (min/Da) | Peak 3, RT/MW (min/Da) | Peak 4, RT/MW (min/Da) |
| Control | 16.812/85.1* | 20.704/4.6* | 24.989/0.2* | — |
| α-CD | 15.263/272* | 17.073/70.0* | 19.966/8.0* | 0.2* |
| β-CD | 17.312/58.5* | 20.484/5.4* | 24.828/0.2* | — |
| γ-CD | 17.663/44.9* | 20.926/3.9* | — | — |

*indicates values below the linear range of the GF column.

As shown in Tables 1 and 2, above, the values indicate that none of the major TANC proteins have broken away from the complex structure. The small molecular masses of the degraded portions of the ANC complex are significantly below the lower limit of the linear range of the GF column. The calculated molecular masses indicate by virtue of the very small molecular masses that the complex is still intact.

Presence of DNA/RNA

Addition of Rnases to the TANC solution indicated NO presence of RNAs or DNAs. The addition of the nucleases was monitored spectrophotometrically at 260 nm for an increase in absorbance as the nucleotides comprising any RNA/DNA present were released from their tertiary structure. While an increase in absorbance was observed (0.002 increase over 3 hours) it was determined that such a small increase could not account for the presence of RNAs or DNAs in any significant concentration.

Example

Preparation of *C. botulinum* Type A

The *C. botulinum* Type A (strain Hall) complex was prepared by the method described in Cai et al. Enhancement of the Endopeptidase Activity of *Botulinum* Neurotoxin by Its Associated Proteins and Dithiothreitol, *Biochemistry,* 1999, 38, 6903-6910, the entire contents of which are incorporated herein by reference. The purified Type A complex was subjected to a buffer exchange using a 5 mL Sephadex G-25 column equilibrated with 10 column volumes of 10 mM sodium phosphate, pH 7.4. The Type A complex was determined to have a typical subunit makeup by SDS-PAGE analysis. The Type A complex, at physiological pH of 7.4, was diluted to a 0.75 mg/mL concentration and 1 mL aliquots were placed into eight 1.5 mL microcentrifuge tubes.

1.5 mg $mL^{-1}$ solutions of the Type A *Botulinum* neurotoxin complex at both 25° C. and 4° C. were analyzed by high performance liquid chromatography using a gel filtration (size exclusion) column (HPLC-GF) both in the presence and absence of 0.1 mM α-, β-, or γ-cyclodextrin in the solution. The WATERS HPLC system was equipped with a Waters 996 Photodiode Array (PDA) detector and dual Waters 515 HPLC pumps. The Waters pump system was integrated by a Waters Pump Control Module and controlled by Waters Millennium Software. The sample was introduced to the system via a Rheodyne 7725I Manual Injection System. The column used for separation of the sample was a Waters Protein Pak 300SW (4.6×300 mm). The buffer conditions used for each separation attempt will be listed below.

Standard Curve Generation

The gel filtration standards (Sigma Chemical Co.) were used to determine the molecular mass standard curve for the Protein Pak column. The buffer system used for the standard curve determination was a 10 mM sodium phosphate buffer, pH 7.4. The results from the standard curve determination are listed in Table 1 below. The equation of the line determined from a plot of Log Molecular Mass versus $V_{et}/V_{ot}$ was calculated to be y=−1.7417x+7.399, $R^2$=0.9398.

TABLE 1

Gel Filtration Standards

| Standards | Mass (Da) | $V_e$ (min) | $V_e/V_o$ | Log [Mass] |
|---|---|---|---|---|
| Blue Dextrin | 2,000,000 | 7.878 | — | — |
| Thyroglobulin | 669,000 | 7.884 | 1.001 | 5.825 |
| β-amylase | 200,000 | 8.862 | 1.125 | 5.301 |
| Alcohol dehydrogenase | 150,000 | 9.693 | 1.230 | 5.176 |
| Carbonic anhydrase | 29,000 | 13.514 | 1.715 | 4.462 |

Neurotoxin A Complex Analysis

The results from the HPLC-GF analysis indicate that it is possible to stabilize the *botulinum* neurotoxin and its complexing NAPs at physiological pH. In 50 mM sodium phosphate buffer, pH 6.8, 85% of the protein remained in complex form. A lower % complex was found in a 10 mM sodium phosphate buffer, pH 7.4, (~70%). The lower % complex at a pH of 7.4 is due to the introduction of the complex directly into the new buffer system. Results similar to that of the pH 6.8 buffer system would be the result if the *botulinum* toxin and NAPs were dialyzed into the pH 7.4 buffer prior to introduction into the HPLC-GF system.

Figure 10:
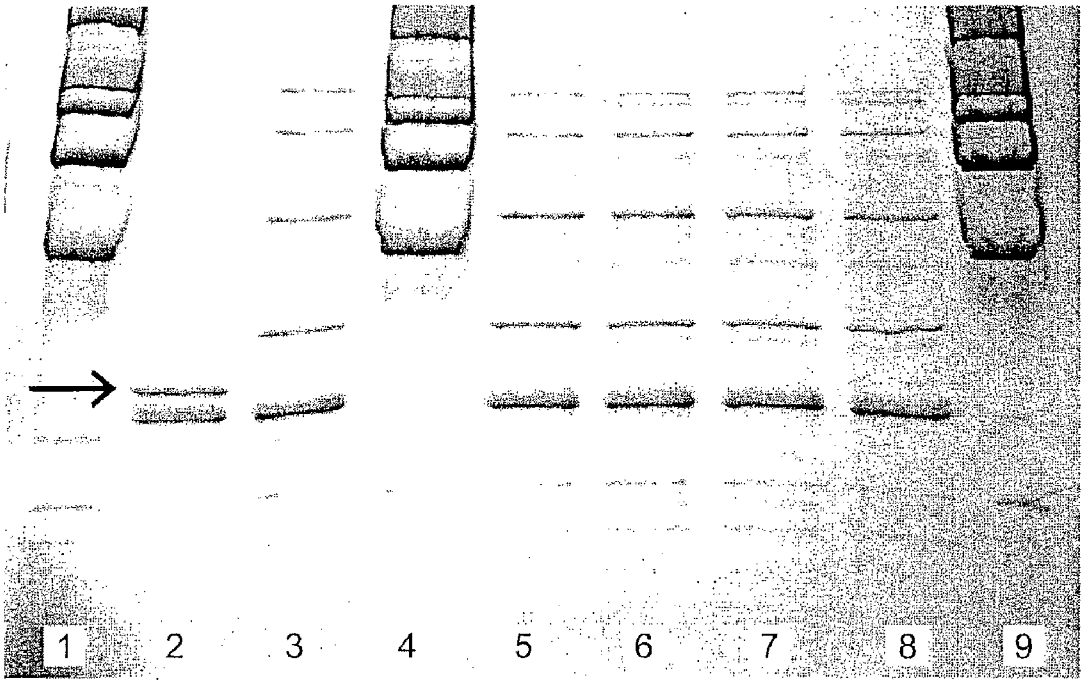
FIG. 10 illustrates SNAP 25 cleavage by Type A Complex at 6 weeks.

Further, stability studies of the endopeptidase activity of Type A Neurotoxin Complex (TANC) were performed at 5° C. and 25° C. in the presence and absence of alpha-cyclodextrin. The results of the study suggest that over a six-week period TANC remained enzymatically active, both in the presence and absence of 0.1 mM alpha cyclodextrin at 5° and 25° C. An electrophoresis analysis of the proteolysis (endopeptidase) product of type A *botulinum* neurotoxin substrate, SNAP-25 (intact SNAP-25 shown with arrow in lane 2) is illustrated in FIG. 10. After treatment with 150 nM TANC (lane 3), the intact SNAP-25 band disappears. Similar results were obtained for TANC stored at 5° C. in 10 mM sodium phosphate buffer, pH 7.4, with (lane 6) or without any α-cyclodextrin (lane 5). Endopeptidase activity was also retained at 25° C. (lanes 7&8).

Figure 11:
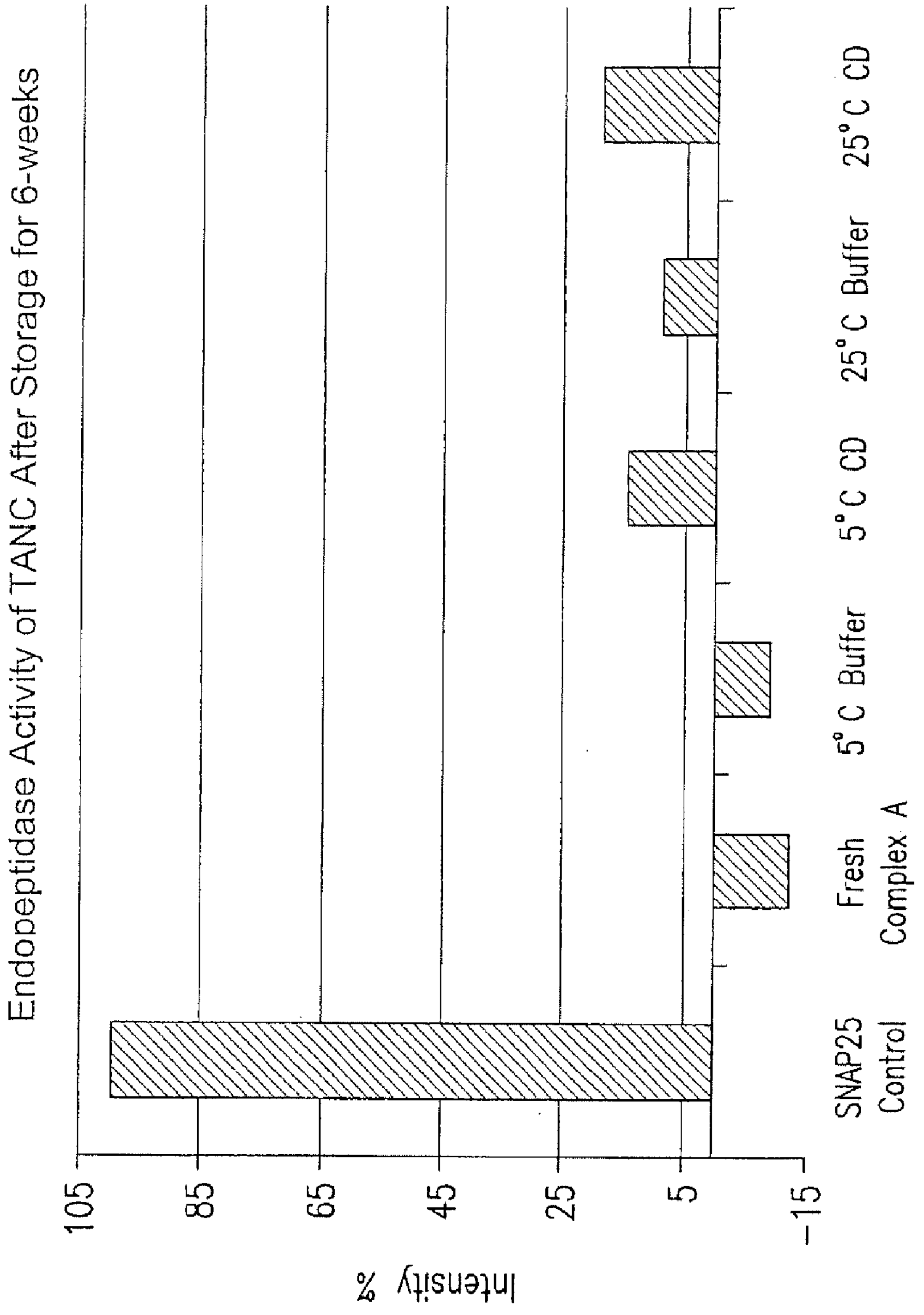
FIG. 11 illustrates endopeptidase activity of TANC after storage for 6 weeks.

FIG. 11 depicts a graphical representation of the endopeptidase activity under different storage conditions. As shown, the endopeptidase activity of TANC in each storage condition remains high. Negative intensity of SNAP-25 intensity in TANC and TANC stored at 5 C in buffer indicates error in the intensity determination of the protein band corresponding to the SNAP-25. The endopeptidase activity of TANC in each condition tested was therefore identical with the experimental error.

The methods and systems of the present invention, as described above and shown in the drawings, provide for a stabilized *C. Botulinum* neurotoxin complex.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A stabilized neurotoxin composition comprising:

a *botulinum* neurotoxin; and a cyclodextrin having cyclic multicyclopyranose units connected by alpha-(1-4) linkages, wherein the cyclodextrin and the *botulinum* neurotoxin form an inclusion complex, wherein the composition has a shelf life of at least four weeks.

2. The composition of claim 1, wherein the cyclodextrin and *botulinum* neurotoxin are present in a molar ratio of at least 25:1 to 50:1.

3. The composition of claim 1, wherein about 55% to about 80% of the *botulinum* neurotoxin remains as the complex for a period of at least 2 weeks.

4. The composition of claim 1, wherein the *botulinum* neurotoxin has about 2% to less than 65% degradation over a period of time of about 23 weeks at storage temperatures that are between 4° C. and 25° C.

5. The composition of claim 1, wherein the botulinum toxin is selected from the group consisting of *botulinum* toxin types A, B, C, D, E, F, and G.

6. The composition of claim 1, wherein the *botulinum* toxin is purified prior to forming the complex.

7. The composition of claim 1, wherein the cyclodextrin is α-cyclodextrin, β-cyclodextrin, or γ-cyclodextrin.

8. The composition of claim 1, wherein the cyclodextrin is present in a stabilizing solution that further comprises a phosphate buffer.

9. The composition of claim 8, wherein the buffer is sodium phosphate and the pH of the solution is about 6.8 to about 7.6.

10. The composition of claim 1, in the form of an injectable solution, or dried preparation.

11. A stabilized neurotoxin composition comprising:

a *botulinum* neurotoxin; and a cyclodextrin, wherein the cyclodextrin and the *botulinum* neurotoxin are present in a molar ratio of at least 25:1 to 50:1 to form a complex that exhibits improved stability compared to the neurotoxin alone as evidenced by a shelf life of at least four weeks with about 55% to about 80% of the *botulinum* neurotoxin remaining as the complex for a period of at least 2 weeks and by exhibiting less than 65% degradation over a period of time of about 23 weeks at storage temperatures that are between 4° and 25° C.

12. The composition of claim 11, wherein the botulinum toxin is selected from the group consisting of *botulinum* toxin types A, B, C, D, E, F, and G.

13. The composition of claim 11, wherein the botulinum toxin is *botulinum* toxin type A, the cyclodextrin is α-cyclodextrin, β-cyclodextrin, or γ-cyclodextrin, and the complex is in the form of an injectable solution or dried preparation.

* * * * *